United States Patent [19]

Marciel

[11] Patent Number: Plant 6,584

[45] Date of Patent: Feb. 7, 1989

[54] ROSE PLANT NAMED DE VROJO

[75] Inventor: Stanley G. Marciel, Pleasanton, Calif.

[73] Assignee: DeVor Nurseries, Inc., Pleasanton, Calif.

[21] Appl. No.: 70,731

[22] Filed: Jul. 7, 1987

[51] Int. Cl.[4] ..... A01H 5/00

[52] U.S. Cl. ..... Plt./10

[58] Field of Search ..... Plt./10

*Primary Examiner*—James R. Feyrer

*Attorney, Agent, or Firm*—Charles W. Rummler

[57] ABSTRACT

A new miniature rose variety distinguished by the solid Cardinal Red coloration of the rose as seen in a face view of the flower and the purplish Spiraea Red coloration of the back side of the flower, as well as by the continuous and profuse year-around blooming habit of its small, well-formed flowers borne singly on sturdy, upright stems; and by its vigorous, bushy, free-branching growth habit reaching a height of about eight inches at twelve weeks and having a floral lasting quality of from twelve to fourteen days as a small pot plant grown either indoors or outdoors.

1 Drawing Sheet

BACKGROUND OF THE INVENTION

This new miniature rose plant resulted as a selected seedling produced by me at Watsonville, Calif., by crossing the red miniature variety 'Scarlet Sunblaze' (U.S. Plant Pat. No. 4,681) with the red polyantha 'Rhumba' (U.S. Plant Pat. No. 1,919) as the pollen parent with the object of producing a nice, red, full miniature rose that can be grown in the house or outdoors in a small pot. The selected seedling appearing to possess all of the desired qualities of strong, vigorous, bushy and rapid growth, and free production of well-shaped blooms, I reproduced this new plant by budding, through several successive generations, at Watsonville, which clearly demonstrated that the novel and desirable characteristics of the new plant would hold true from generation to generation and appeared to be firmly fixed.

DESCRIPTION OF THE DRAWING

My new rose plant is illustrated by the accompanying photographic drawings, in which the uppermost view shows a fully grown potted plant in full bloom and in which the lower view shows a newly opened flower and a fully opened mature bloom, together with front and back side views of typical leaves and a budded stem illustrating its branching character, the colors shown being as nearly true to those specified herein as it is reasonably possible to obtain by professional photographic procedures.

DESCRIPTION OF THE NEW VARIETY

The following is a detailed description of my new rose plant based upon observation of greenhouse grown plants at Watsonville, Calif., the color designations being according to The R.H.S. Colour Chart published by The Royal Horticultural Society of London, England.

THE PLANT

Origin: Seedling.

Parentage:

*Seed parent.*—'Scarlet Sunblaze' (U.S. Plant Pat. No. 4,681).

*Pollen parent.*—'Rhumba' (U.S. Plant Pat. No. 1,919).

Classification:

*Botanic.*—Miniature.

*Commercial.*—Miniature for House or Border Plants.

Form: Upright, compact miniature bush.

Growth rate: Vigorous for a mini plant.

Height: About 10 inches (198 mm.).

Main stem length: About 198 mm. from the potting material surface in a 10 c. pot.

Color: Green, 143A.

Branching character: Free branching.

Growth habit: Vigorous, sturdy and bushy.

Foliage:

*Quantity.*—Abundant.

*Number of leaves.*—7 to 9 from hook on flower stem.

*Size of leaf.*—About 58 mm. long on a five-leaf rachis.

*Leaflets.*—Number: 3 to 5. Size: About 26 mm. long. Shape: Ovate with denticulate margins.

*Texture.*—Semi-leathery.

*Aspect.*—Smooth and glossy.

*Color.*—Upper side — Green, 136B. Under side — Yellow Green, 147B.

*Stipules.*—Adnate with thread-like auricles.

*Petiolule.*—1 mm.

*Rachis.*—About 35 mm. long for five leaflets and about 11 mm. long for three leaflets.

*Petioles.*—Length: About 11 mm.

*Ribs and veins.*—Depressed on under side.

Thorns: The plant does have thorns.

*Size.*—About 3 mm.

*Color.*—Greyed Orange, 166D.

THE BUD

Size: Miniature.

*Diameter.*—About 7 mm.

*Length.*—About 10 mm.

Form: Urn-shaped with pointed tip.

Rate of opening: About five days.

Sepals:

*Number.*—Five.

*Character.*—Reflexing; one sepal tends to leaf and the sepals curl back when the flower opens.

*Color.*—Inside — Green, 138B, with silver hairs. Outside — Green, 143A.

Calyx:

*Shape.*—Pear-shaped.

*Size.*—Small.

*Splitting.*—The calyx does not split.

*Aspect.*—Smooth.

Peduncle:

*Length.*—About 20 mm. and slightly hairy.

*Character.*—Ridged and slender.

*Color.*—Green, 143A.

THE FLOWER

Blooming habit: Continuous and profusely the year around; in the Fall, the plant blooms well under greenhouse conditions.

Size of bloom: Small.

*Diameter.*—About 38 mm.

*Depth.*—About 10 mm.

Borne: Singly.

Form: Flat.

Petalage: About 25 to 28.

*Number of florets.*—Five.

*Arrangement.*—Imbricated.

*Form.*—Reflexed with small margins and abrupt points at apex.

*Texture.*—Leathery.

*Appearance.*—Velvety.

*Color.*—Outer petals: Body — Red, 53B. Base — White, 155A. Color measurement — Red, about 16 mm.; white, about 2 mm. Reverse side — Red Purple, 63A, with white base. Color measurement — 63A, about 16 mm., white, about 2 mm. Inside petals: Body — Red, 53B. Base — White, 155A. Color measurement — Red, about 11 mm.; white, about 2 mm. Reverse side — Red Purple, 63A, with White, 155A. Color measurement — 63A, about 11 mm.; white about 2 mm.

*Petaloids.*—Number: Three. Size: 6 mm. Color: Red, 63B.

*Peduncle.*—Length: About 22 mm. Color: Green, about 143A. Character: Sturdy and upright.

Persistence of flower: The petals hang on and dry.

Disease resistance: Moderately resistant to mildew, rust and spot as observed in greenhouse in Pleasanton, Calif., and Watsonville, Calif.

Fragrance: Slight.

Lasting quality: About twelve to fourteen days on the plant.

REPRODUCTIVE ORGANS

Stamens:

*Number*—About 85.

*Arrangement.*—Introrsed.

*Anthers.*—Size: About 4 mm. Color: Greyed Oranged, 164C.

*Filaments.*—Length: About 4 mm. Color: Greyed Orange, 165C.

*Pollen.*—Color: Greyed Orange, 164B.

Pistils:

*Number.*—About 30.

*Styles.*—Length: About 3 mm. Color: Greyed Orange, 165D.

Stigmas:

*Color.*—Yellow Orange, 18B.

Character of ovaries: Small funnel-shaped with rounded edges and with silver threads covering the entire ovary.

This new variety most nearly resembles 'Scarlet Meillandina'. The new variety is a better balanced plant, however, with more even growth and excellent winter propagation.

I claim:

1. The new and distinctive variety of miniature rose plant and parts thereof, substantially as herein shown and described, characterized by its profuse and continuous production of Cardinal Red flowers of small size and having a vigorous, upright, free-branching and rapid growth rate habit.

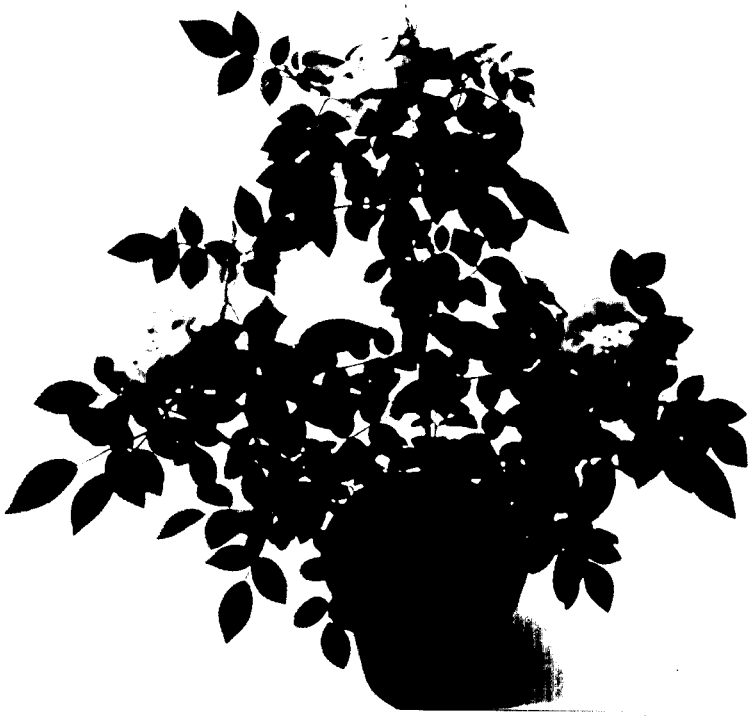
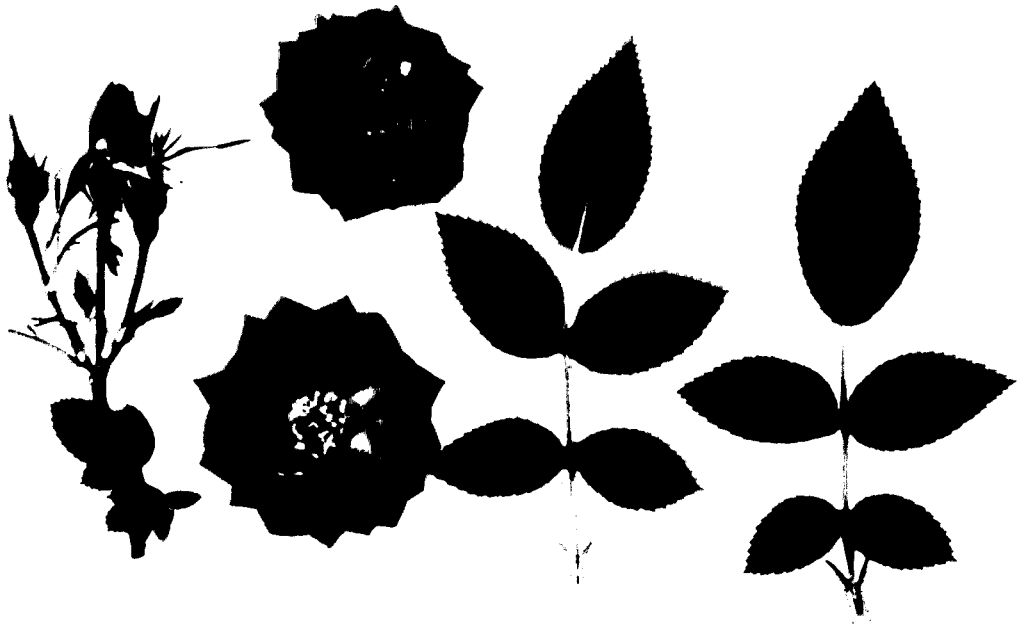

* * * * *